(12) United States Patent
Ayanruoh (10) Patent No.: US 11,172,825 B1
(45) Date of Patent: Nov. 16, 2021

(54) HANDHELD MULTIPURPOSE MEDICAL DIAGNOSTIC INSTRUMENT FOR EXAMINATION OF EARS, EYES, NOSE, THROAT, AND BODY TEMPERATURE

(71) Applicant: Stephen T. Ayanruoh, Yonkers, NY (US)

(72) Inventor: Stephen T. Ayanruoh, Yonkers, NY (US)

( * ) Notice: Subject to any disclaimer, the term of this patent is extended or adjusted under 35 U.S.C. 154(b) by 466 days.

(21) Appl. No.: 15/878,200

(22) Filed: Jan. 23, 2018

Related U.S. Application Data (60) Provisional application No. 62/449,144, filed on Jan. 23, 2017.

(51) Int. Cl.
| | |
|---|---|
| *A61B 5/00* | (2006.01) |
| *A61B 3/14* | (2006.01) |
| *A61B 1/227* | (2006.01) |
| *A61B 3/12* | (2006.01) |
| *A61B 5/01* | (2006.01) |
| *A61B 5/12* | (2006.01) |

(52) U.S. Cl.
CPC ............ *A61B 5/0077* (2013.01); *A61B 1/227* (2013.01); *A61B 3/12* (2013.01); *A61B 3/14* (2013.01); *A61B 5/0082* (2013.01); *A61B 5/01* (2013.01); *A61B 5/12* (2013.01); *A61B 5/7435* (2013.01); *A61B 2560/0214* (2013.01); *A61B 2560/0431* (2013.01)

(58) Field of Classification Search
CPC ..... A61B 5/0077; A61B 5/7435; A61B 1/227; A61B 3/12; A61B 5/01; A61B 5/12; A61B 3/14; A61B 5/0082; A61B 2560/0431; A61B 2560/0214

USPC .......................................................... 600/474
See application file for complete search history.

(56) References Cited

U.S. PATENT DOCUMENTS

| | | | |
|---|---|---|---|
| 5,595,289 A * | 1/1997 | Kurek .................. | H01H 23/143 200/315 |
| 5,701,094 A | 12/1997 | Simmons et al. | |
| 6,319,199 B1 | 11/2001 | Sheehan et al. | |
| 6,381,484 B1 | 4/2002 | Ayanruoh | |
| 7,137,948 B2 | 11/2006 | Tsai | |
| 7,680,438 B2 | 3/2010 | Yano | |
| 2003/0171655 A1 | 9/2003 | Newman et al. | |
| 2005/0043588 A1* | 2/2005 | Tsai ........................ | A61B 1/07 600/160 |
| 2005/0171399 A1 | 8/2005 | Rich et al. | |
| 2006/0026784 A1* | 2/2006 | Moskovich ........ | A46B 15/0081 15/110 |
| 2014/0046192 A1* | 2/2014 | Mullin ................... | H05K 13/00 600/474 |

(Continued)

FOREIGN PATENT DOCUMENTS

DE           3410201 C2 *   9/1987   ............. G02B 21/26

*Primary Examiner* — Serkan Akar
*Assistant Examiner* — Renee C Langhals
(74) *Attorney, Agent, or Firm* — Rashauna Norment (57) ABSTRACT

A handheld, multipurpose medical diagnostic instrument capable of examining a patient's ears and eyes, detecting the patient's body temperature, capturing the patient's photograph for a patient profile and capturing the target of interest, and transmitting the collected data to an external device. The obtained images, video, and/or data may be displayed on at least one display screen for viewing in real time or for later viewing.

14 Claims, 4 Drawing Sheets

(56) References Cited

U.S. PATENT DOCUMENTS

2015/0092099 A1* 4/2015 Shen .................... G01J 3/0237
                                                                 348/349
2016/0290869 A1* 10/2016 Frank .................... G01J 5/0265
2019/0038135 A1*  2/2019 Lee ......................... A61B 3/12

* cited by examiner

HANDHELD MULTIPURPOSE MEDICAL DIAGNOSTIC INSTRUMENT FOR EXAMINATION OF EARS, EYES, NOSE, THROAT, AND BODY TEMPERATURE

CROSS-REFERENCE TO RELATED APPLICATIONS

This application claims the benefit of U.S. Provisional Application No. 62/449,144, filed Jan. 23, 2017, and the provisional application is incorporated by reference herein.

FEDERALLY SPONSORED RESEARCH AND DEVELOPMENT

Not applicable.

BACKGROUND OF THE INVENTION

1. Field of the Invention

The present invention generally relates to the field of medical instruments. More particularly, the invention relates to a handheld, multipurpose medical diagnostic instrument capable of examining a patient's ears, eyes, nose, and mouth; detecting the patient's body temperature, capturing the patient's photograph for a patient profile and for a target of interest; and transmitting the collected data to an external device. The obtained images and information may be displayed on at least one display screen for viewing in real time or for later viewing.

2. Description of Arguably Related Art Including Information Disclosed for 37 CFR 1.97 and 1.98

Medical personnel often use various handheld medical diagnostic instruments during patient examination. Examples of the different handheld medical diagnostic instruments are otoscopes for ear, nose and throat examination, ophthalmoscopes for eye examination, illuminators, and thermometers for detecting body temperature. Some of these instruments include a display screen and may further incorporate various examining and diagnostic tools into the same instrument. Disadvantages and limitations of these instruments include inadequate lighting, the inability to capture and review images or data in real time on an external device or on the instrument itself, or a housing that has an uncomfortable configuration and arrangement of the components. Some instruments are expensive to purchase and maintain which may be cost prohibitive to smaller clinics or in the field. Many of these instruments do not provide a sufficient handheld, integrated medical diagnostic instrument for examining the eyes and the ears, for obtaining the patient's body temperature using a contactless thermometer or temperature sensor, and for capturing the target of interest or the person's image.

Disadvantages and limitations of these devices include a small view display screen, the inability to capture and review images in real time on an external viewing device, uncomfortable holding or arrangement and straining on personnel during examination.

U.S. Pat. No. 7,137,948 issued to Tsai discloses a medical instrument used in patient diagnostic, inspection, and examination. The instrument includes a body having a pistol-shaped handgrip and a frusto-conical speculum, with the speculum having a nose with a distal opening disposed along an axis of examination. The body also includes an image capture device and a light source. The image capture device includes an autofocus module. A video display is housed with the body and a wireless communication module is disposed within the instrument.

U.S. Patent Application Publication No. 2005/0171399 filed by Rich et al. discloses a portable otoscope video adaptor and viewing unit for examination of the ears, eyes, nose, and throat and for increasing the size of the obtained view. Both the patient's temperature and a recorded view of each eardrum can be obtained in a minimum amount of time. The device contained a built-in camera and thermometer recorder in a hard-shell plastic case adaptable for attachment onto a Welch Allyn or Heine type otoscope head. The device had a plurality of buttons for turning the unit on and off, starting the video camera, turning off internal light source when used in stand alone mode, freeze-frames of images, and for taking temperature of the eardrum. The temperature reading is shown on the LCD. The camera, LCD, and video recorder use pre-existing technology. The lens of the camera changes to allow focus on the eardrum with the otoscope or on the retina with the ophthalmoscope. The device has built-in software for recording or taking still images.

Some of the previously available instruments have limitations that pose a challenge during examination, for example, many lack real time viewing of procedures, adequate illumination, or adding a building a comprehensive patient profile or small viewing screens. Some instruments are expensive to purchase and maintain which may be cost prohibitive to smaller clinics or in the field.

Therefore, a need exists for an improved handheld medical diagnostic instrument having photograph or video capturing technology that enables a user (or practitioner) to observe both the patient and the instrument while viewing the image captured on a display screen.

A need exists for an improved handheld multipurpose medical diagnostic instrument that is capable of performing more than one diagnostic procedure.

A need exists for an improved handheld multipurpose medical diagnostic instrument that enables a user to conduct multiple diagnostic procedures and examination of a patient's ears, eyes, or other orifices or body members, body temperature, and of capturing that information during examination while using a single device.

A need exists for an improved handheld multipurpose medical diagnostic instrument that is cost-effective, lightweight and portable.

A need exists for an improved handheld multipurpose medical diagnostic instrument that provides simultaneous transmission of the obtained information and viewing the collected information in real time or for later viewing.

A need exists for an improved handheld multipurpose medical diagnostic instrument that includes an examining assembly for examining the ear and the eye, a contactless temperature sensor for obtaining the patient's body temperature, and a capturing means for capturing images during examination and for capturing images of the patient's physical appearance for a profile.

SUMMARY OF THE INVENTION

The invention is a multipurpose medical apparatus, and more specifically, a handheld multipurpose medical diagnostic instrument for examining multiple areas of a patient or a subject while using a single medical tool. The apparatus comprises (includes or has):

(a) an examining assembly for examining a patient's ears, the eyes, and any other orifice, cavity, or body member, for example, the mouth or nasal cavity;

(b) a contactless temperature sensing mechanism for obtaining a patient's body temperature without touching the patient's skin;

(c) a capturing means for capturing at least the image or photograph of the patient or a target of interest;

(d) a data collecting means for collecting the data obtained during the examination;

(e) a transmitting means for transmitting data to an external source; and (f) a housing for containing the examining assembly, the temperature sensing mechanism, the data collecting means, the capturing mechanism, and the transmitting means.

The apparatus further includes at least one display screen for viewing the images and information obtained during examination, a light source, and a power source. The external source (or external device) receives the transmitted data and may include software for analyzing, storing, and reporting on the collected data.

The examining assembly is used as an otoscope and an ophthalmoscope. The examining assembly may also include a focusing mechanism, a light source, and a power source. The contactless temperature sensing mechanism is essentially a contactless thermometer having a sensor, preferably an infrared sensor. The focusing mechanism is essentially a camera with a lens that cooperates with the examining assembly to magnify or minimize the view of the target of interest or of the patient. The focusing mechanism also includes a means for adjusting the focal length of the lens. The compact, lightweight, and portability of the apparatus is helpful to the user, typically a medical practitioner, and allows flexibility and immediate access to the patient. The apparatus may be used in a variety of settings, including, but not limited to, an emergency room, a clinic, a hospital, and in the field or other non-hospital setting. The data may be stored in the apparatus until transferred or otherwise shared with an external source. The data may be transmitted wirelessly or through conventional wired connection to the external source, such as a computer, laptop, server, or other device.

The arguably relevant patent references, taken either alone or in any proper combination, fail to disclose or teach the particular arrangement, structure, and location of all of those elements as claimed.

It is an object of the invention to provide a handheld multipurpose medical diagnostic apparatus that allows a user to conduct different medical examinations while using a single medical tool.

It is an object of the invention to provide a handheld multipurpose medical diagnostic apparatus that allows a user to provide simple, quick, and easy examination of patients.

It is an object of the invention to provide an improved handheld multipurpose medical diagnostic instrument which is capable of performing more than one diagnostic procedure.

It is an object of the invention to provide an improved handheld multipurpose medical diagnostic instrument which enables a user to conduct diagnostic and examination of a patient concerning ear, eye, temperature, and capturing images during examination using a single device.

It is an object of the invention to provide an improved handheld multipurpose medical diagnostic instrument that is cost-effective, light-weight and portable.

It is an object of the invention to provide an improved handheld multipurpose medical diagnostic instrument that provides simultaneous transmission of the data and images for viewing the collected information in real time.

It is an object of the invention to provide an improved handheld multipurpose medical diagnostic instrument that includes an examining assembly for examining the ears and the eyes, a contactless temperature sensing mechanism, and a capturing means for capturing images during examination and for capturing images of the patient's physical appearance for a profile.

These and other aspects, objects, embodiments, and advantages of the invention will become apparent from the accompanying drawing and the following detailed description of the preferred embodiments of the invention.

BRIEF DESCRIPTION OF THE SEVERAL VIEWS OF THE DRAWING

The invention may be more readily described by reference to the accompanying photographic, schematic drawing figures, and the following description of the drawing figures. The reference numbers apply to each embodiment of the invention. In the drawing.

Figure 8:
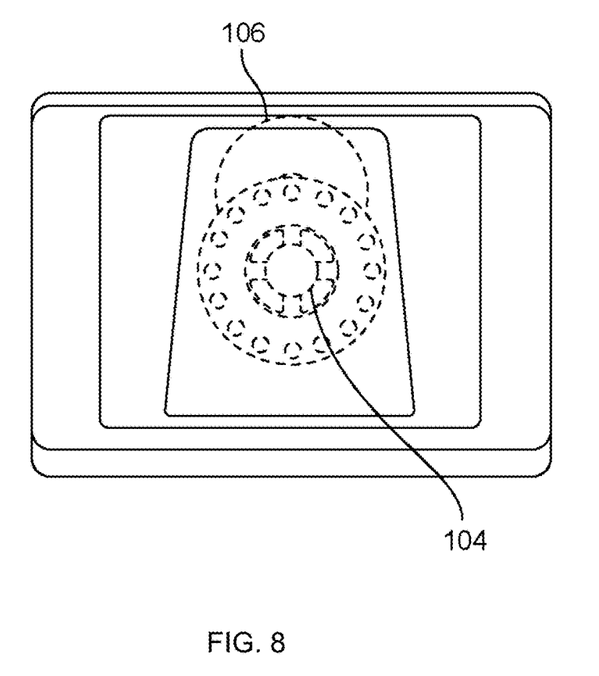
FIG. 8 is an exploded view of FIG. 3 thereof, also showing internal components within the multipurpose medical diagnostic instrument
Figure 9:
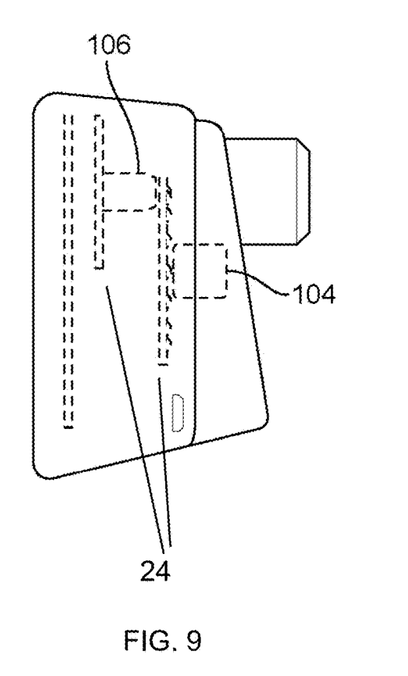
FIG. 9 is an exploded view of FIG. 2 thereof, also showing internal components within the multipurpose medical diagnostic instrument.

The broken lines shown in FIGS. 8 and 9 represent internal components within the multipurpose medical diagnostic instrument.

DETAILED DESCRIPTION OF THE INVENTION

The present invention, preferred embodiments of the invention, and the accompanying drawing figures as described herein should not be construed as limited to the illustrated drawing. Rather the illustrated embodiment(s) are detailed to provide a thorough disclosure suitable to convey the scope of the invention to those skilled in the art. For the sake of simplicity, the conjunctive "and" may also be taken to include the disjunctive "or," and vice versa, whenever necessary to give the claims of this patent application the broadest interpretation and construction possible. Likewise, when the plural form is used, it may be taken to include the singular form, and vice versa.

Referring more particularly to the drawing by characters of reference, FIGS. 1-9 depict an improved handheld multipurpose medical diagnostic instrument that comprises (includes or has): an examining assembly for examining a patient's ears and the eyes and for capturing at least the image of the patient or a target of interest; a temperature sensing mechanism for obtaining a patient's body temperature; a data collecting means for collecting the data obtained during the examination; a transmitting means for transmitting data to an external source; and a housing for containing the examining assembly, the temperature sensing mechanism, the data collecting means, and the transmitting means. The target of interest may be item or structure on or about the patient to be examined, for example, the eyes, the ear canal, the nasal cavity, the mouth or other body member or orifice, or the person's face in general.

In another embodiment, the invention is an improved multipurpose medical diagnostic instrument for examining a patient's ears, eyes, or other orifice or body member, for obtaining the patient's body temperature, and for capturing a target of interest. The medical instrument comprises (a) a housing having a head having a first display screen, a second display screen, and a contoured handle, with the housing supporting the mechanical and electronic components of the instrument; (b) an examining assembly having a lens, a gear train operable by an electric motor, and a camera module, with the data and images displayed on a first display screen; (c) a contactless temperature sensing mechanism having an infrared sensor for obtaining a patient's body temperature, with the temperature results displayed on a second display screen; (d) a plurality of illumination members; and (e) a data collecting means for collecting the obtained data and cooperating with a transmitting mechanism for transmitting or receiving the data.

The housing 1 has a head 2 and a handle 3. The housing contains the instrument's mechanical components, electrical components, and a power source or power supply. The housing is compact and lightweight. The handle is contoured to comfortably fit in the user's hand. In one preferred embodiment, the head and the handle of the housing is a single unit, with at least a portion of the housing having a removable portion or member for accessing the power source or power supply, namely, a battery. Alternatively, the head and the handle are two separate units that are coupled together to form the housing. Also here, at least a portion of the housing has a removable member for accessing the power source. The exterior of the housing may be cleaned and disinfected, as needed. The contouring and configuration of the housing eliminates excess material for a more cost-effective, portable, compact apparatus.

The head 2 of the housing 1 has a front, a rear, and two sides. The head of the housing contains most if not all of the mechanical components of the examining assembly, the focusing mechanism, and the temperature sensing mechanism. The head further contains most if not all of the electronic components for collecting the data obtained and for transmitting that data to an external source.

Figures 1, 2:
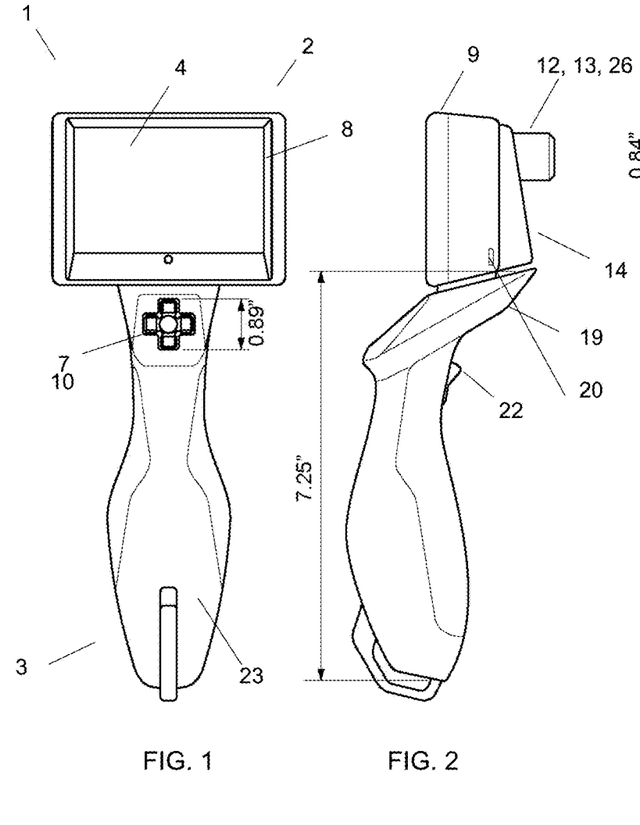
FIG. 1 is a front plan view of a multipurpose medical diagnostic instrument, showing my new design.
FIG. 2 is a side elevation view of FIG. 1 thereof.
Figure 4:
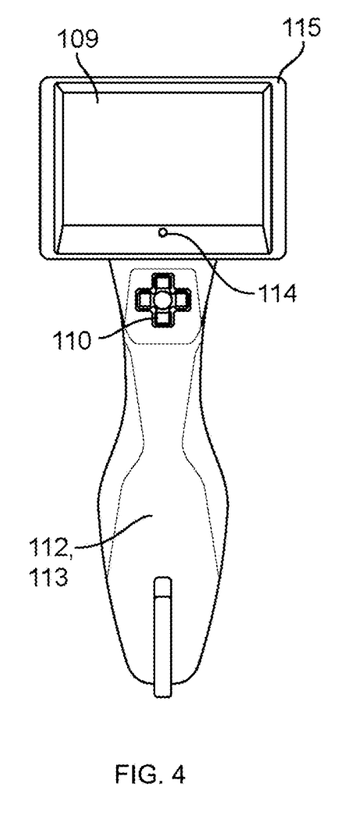
FIG. 4 is another front plan view of FIG. 1 thereof.
Figure 5:
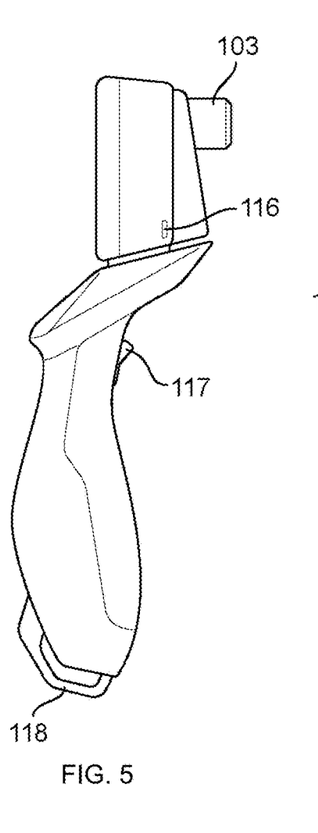
FIG. 5 is another side elevation view of FIG. 1 thereof.
Figure 7:
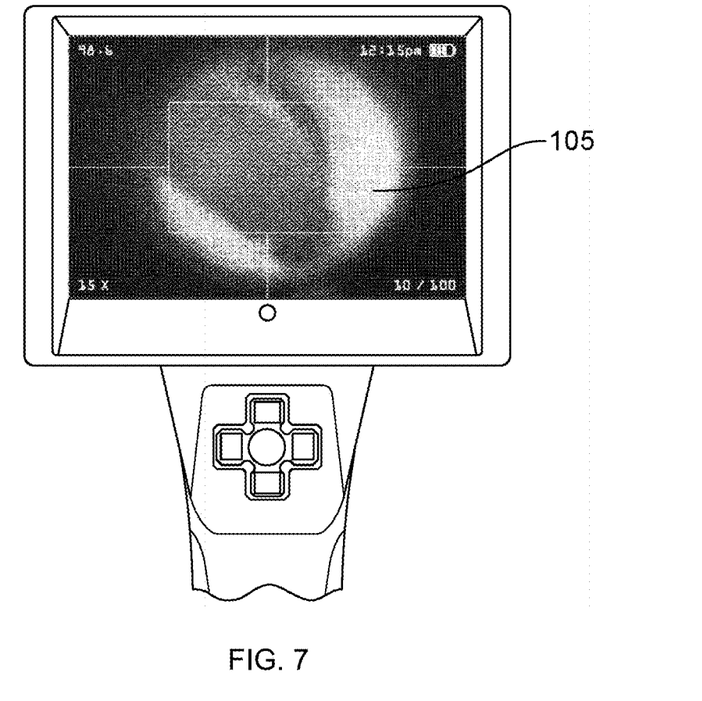
FIG. 7 is an exploded view of FIG. 1 thereof, shown in use.

FIGS. 1, 4, and 7 depict the front of the head 2 having at least one display screen 4 for displaying the various data in real time and for later review. A second display screen may be provided to display the body temperature results that are obtained from the temperature sensing mechanism. In one embodiment, the head of the housing has a first display screen and a second display screen, with the second display screen preferably positioned below the first display screen. Preferably, the second display screen is smaller than the first display screen. Alternatively, the second display screen may be located at the handle or body of the housing. The first display screen is the primary viewing member for viewing the images, data, or other information. The second display screen allows for a 4 digit, 7 segment body temperature reading result. At least one of the display screens may be an LCD display; however, any other suitable display screen or viewing member may be used. The images of the patient or of the patient's eyes, ears, nasal cavity, mouth, or other orifice or body member can be easily viewed by the user with the display screen.

The front of the head 2 of the housing 1 also includes at least one illumination member or light source 6, and a plurality of buttons 7 for selecting various icons, actions, and menu settings shown on the display screen 4, and for activating the electronic components. The plurality of buttons 7 may be positioned directly on the housing or on a multifunctional directional pad 10. The images, information, and data may be viewed in real time or they may be later retrieved for viewing on the display screen or on an external device. In one embodiment, the information may be viewed simultaneously viewed on the display screen while or after being transmitting to an external device.

In one embodiment, the front of the head has a frame 8 that circumscribes or surrounds the display screen 4. More particularly, the frame 8 has a lip 9 that surrounds the display screen 4 with the frame 8 recessing inwardly. The screen 4 is further recessed. The lower portion of the frame 8 extends downwardly into a substantially U-shaped or semi-circular thumb member 10. The thumb member may have a plurality of buttons for activating the electronic components of the apparatus, including making adjustments to the focusing mechanism of the camera, for capturing images, and for examining the patient. The frame 8 may also include an opening 11 for a light source 6.

The back of the head 2 of the housing 1 has a light source 6 and an examining assembly, namely, a speculum 12 and a retractable lens 13. Inside the back of the housing includes the electronic components, the examining assembly, and the temperature sensing mechanism. In one embodiment, a portion of the back of the head contours downwardly to a base 14 that extends outwardly behind the head. The lower portion of the base has a step or recessed member. The base 14 further circumscribes a hole for receiving the speculum 12 and the lens 13. The base also has a plurality of spaced apart apertures 16 for the light source 6, namely, a plurality of LEDs. The lower portion of the back of the head further defines a bore 17 for receiving the temperature sensing mechanism 18, which is preferably located below the base 14 of the head 2 near the neck 19 of the handle 3.

The sides of the head may include a connection port 20 for connecting an adapter 21 with a cord to the apparatus and to an outlet or an external device, for example, a computer, a laptop, or other mobile device. The sides of the head may also include a power switch member 22 for activating the instrument.

The handle 3 may be integrated into the housing 1, or it may be a separate, connectable handle that is attached to the head of the housing. The handle 3 of the housing has a neck 19 and a body 23. The neck supports the head of the housing. The bottom of the head of the housing contours and tapers inwardly to form the neck before expanding bulbously into the handle. The bottom of the handle of the housing may be substantially flat so that it may stand, or otherwise be placed, in an upright position. The handle may have any configuration, shape, or contouring as long as the apparatus is capable of being handheld. The body of the handle of the housing is contoured to comfortably fit in the user's hand. The handle of the housing may be smaller than the head so as to be suitable for use as a handgrip.

The examining assembly is used to conduct the otoscope and the ophthalmoscope examination. The user may also use the instrument to examine any other part of the body including the nasal cavity and the mouth. The examining assembly includes a focusing mechanism for capturing the small details of the inner ears and the eyes up to the larger image of a patient's face for a profile photograph. More particularly, the examining assembly has at least a gear or gear train 24, an electric motor 25, a lens 13 for selective focus adjustment, a speculum 12, and a camera module 26 for capturing or recording the target of interest. The gear or gear train cooperates with the electric motor to selectively adjust the macro or micro focus of the lens, inwardly or outwardly. The electric motor may be a miniature electric motor that controls the speed or reduction of the gear train. The adjustable lens is used not only to view and/or capture the details of the ears and eyes, but also to take the patient's photograph. The back of the head of the housing 1 may taper into a hole in which the lens 13 can retract or expand within and/or through the hole for the user to view and examine the target of interest, or to capture and record the target of interest.

In an embodiment, the examining assembly, namely, the focusing mechanism, includes a miniature electric motor 25, a gear train 24 having a first larger gear and a second smaller gear, a speculum 12, a retractable lens 13, a threaded shaft, and a camera module 26. The gear train may be used for speed reduction. The larger gear may be located behind an interior plate of the base of the back of the housing, behind the plurality of illuminating members 6. The larger gear adjusts the camera lens inwardly toward and outwardly from the speculum connected at the base of the head of the housing. Here, the focusing mechanism has a substantially tiered conical structure insertable through the larger gear movement of the gear (or gearhead), and consequently the camera lens. The lens may be coupled to the threaded shaft, with the focus adjustable with the gear operable by the electric motor and being selectively controlled by the toggle buttons 7. The camera module may be positioned or coupled to the opposite end of the shaft.

A disposable examining tip may be removably attached to the speculum. More particularly, the disposable tip may be inserted over the speculum during examination, then discarded. When examining the patient, particularly, the ears or eyes, the instrument employs the lens which acts as a magnifying tool. The user inserts the disposable tip over or to the speculum and into the ear or near the eye, adjusts the focus of the lens, and the lighting, if needed, then views the image on the display screen. Images or video can also be captured for later viewing by using one or more of the plurality of buttons 7.

Figure 3:
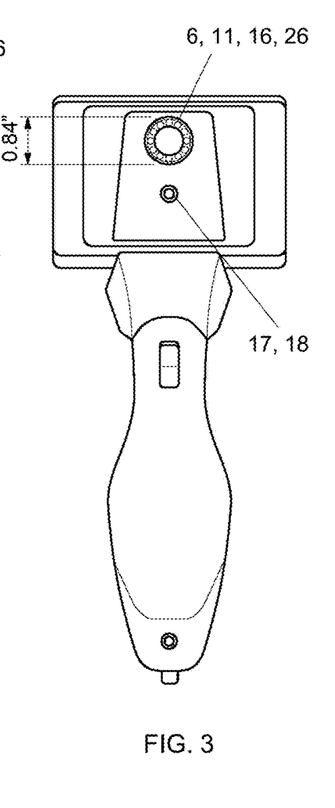
FIG. 3 is a rear plan view of FIG. 1 thereof.
Figure 6:
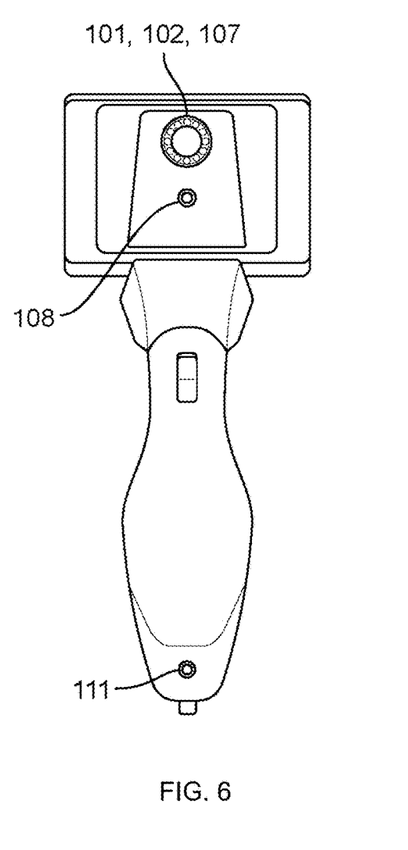
FIG. 6 is another rear plan view of FIG. 1 thereof.

The light source 6 may be one or more of a plurality of illuminating members, for example, one or more LEDs. However, any other suitable light source may be used to illuminate the target of interest. As shown in the figures, when the light source is a plurality of illuminating members, the illuminating members may be arranged in a spaced apart circular or ring pattern about the base of the back of the housing, as shown in FIGS. 3, 6, and 8. At least one LED may also be provided at the front of the head of the housing. The light source may be selectively activated with or without using the examining assembly. The intensity of the illumination is adjustable from dim to bright, and vice versa. In another embodiment, the user may selectively activate one or more of the light sources at any time by selecting the appropriate icon on the display screen.

The temperature sensing mechanism may include a sensor 18 capable of obtaining a patient's body temperature without the need for inserting a thermometer into the patient or directly against the patient's skin. The non-contact temperature sensor may be an infrared sensor or otherwise employ infrared technology. The temperature sensor may be in communication or in connectivity with one of the electronic components within the instrument so that the temperature results may be displayed on the display screen, preferably on the second display screen. The data for the temperature results may also be stored on the instrument as well as transmitted to an external device for later retrieval. The temperature sensor is preferably located at the rear of the head of the housing. The temperature sensor may be activated by pressing the appropriate button on the front of the head of the housing, then selecting the option for taking the patient's body temperature.

The switch member 7 may be a toggle switch, a button, or any other controlling means. The switch member is in communication with the electronic components of the apparatus. The data collecting means may include at least one circuit board coupled to the display screen and to the examining assembly. The data collecting means may further include a memory or data storage means and a processor, each in communication with the circuit board, the display screen, and the transmitting mechanism.

The transmitting mechanism involves capturing and obtaining the image or the target of interest, and selectively transmitting a signal to send that information to the instrument's display screen or to an external device, either simultaneously, alternatively, or sequentially. The image may be stored in the patient's file or folder on the external device. The user may select the information to be transmitted to or received from the external device by selectively choosing the menu options shown on the display screen. In another embodiment, the external device is in communication with the apparatus, with the external device capable of directly accessing the information stored on the apparatus.

The power source or power supply 32 may be battery powered or otherwise connectable to an external electrical source. For example, the apparatus may be connected to an adapter 21, which is coupled to an external device or to an AC/DC outlet for powering the apparatus. The battery may be charged when the adapter is used as the primary power source, or the battery may be replaced or externally recharged. The battery is preferably located inside the handle. Preferably, the battery is a rechargeable lithium polymer battery. Any suitable battery for continued operation of the apparatus may be used. The handle of the housing may further include a chamber for holding the battery. A portion of the handle may be opened to receive or retrieve the battery. The adapter cord may also be connected to another electronic device to download or at least access the data on the instrument. The power supply or power source provides power to operate the mechanical components and electronic components of the apparatus.

In yet another embodiment further as shown in FIGS. 1-9, the handheld multipurpose medical diagnostic apparatus comprises (includes or has) an examining assembly, a light source, a contactless temperature sensing mechanism, a data processing mechanism, a control panel, a power source, and a housing. The examining assembly has a lens assembly, a speculum, a focusing mechanism, and a camera module.

The lens assembly has a rotatable circular plate 101 and a plurality of lenses 102, with the circular plate 101 defining a plurality of spaced apart apertures arranged in a ring or circular pattern. Each of the apertures supports one of the plurality of lenses. Each of the plurality of lenses has a different focal length for selectively magnifying, viewing, or examining at least a patient's face and body, the ear and ear canal, the structure of the eyes, the nasal cavity, and the throat during examination. At least a first of the plurality of lens is a single 3× lens, and at least a second of the plurality of lens is a single 15× lens. A reason for providing multiple lenses, with each lens having a different focal length allows the practitioner to vary the magnification of the obtained image, depending on the type of examination. For example, when the apparatus is used as an ophthalmoscope, viewing the retina and the other parts of the patient's eye structure requires a higher magnification than viewing the ear canal when the apparatus is used as an otoscope. The focal length or magnification of each lens is not limited to only 3× and 15×. The speculum 103 has a proximal opening for use a viewpoint. The speculum is engageable with the lens assembly.

The focusing mechanism is coupled to the lens assembly for rotating the circular plate for selectively switching to a different lens focal length. The focusing mechanism adjusts the focal length or magnification of each of the lens during examination. The focusing mechanism is operable by a motor 104. The motor is a direct drive stepper motor for controlling the lens assembly. The motor is selectively actuated by the control panel 105.

The camera module 106 selectively captures patient information having one or more images and video of the patient's face or body for a patient profile, and one or more images and video of the patient's ear canal, eye structure, nasal cavity, and throat. The examining assembly being capable of being used selectively as an otoscope, an ophthalmoscope, and a camera.

The light source 107 is capable of being used independently and selectively from the examining assembly. The light source is operatively controlled by a control panel. The light source may further have a plurality of illuminating members arranged in a circular pattern similar to the circular or ring pattern of the plurality of lenses. The contactless temperature sensing mechanism 106 obtains a patient's body temperature as data. The contactless temperature sensing mechanism has an infrared sensor in communication with the electronic components and the power source. The temperature reading displayable on the display screen 109, and with the temperature sensing mechanism actuated by the control panel. The data processing mechanism is capable of storing, processing, and retrieving the patient information and data obtained from the examining assembly and the temperature sensing mechanism. The data processing mechanism is also capable of transmitting and receiving the patient information and data to and from an external device. The data processing mechanism provides review of patient information and data on the display screen directly from the apparatus memory or from an external device on an independent display screen or on the apparatus' display screen. The external device may be a laptop, a computer, a mobile phone. The external device may also include cloud storage. The housing includes a port for data transfer, preferably, a micro USB port 116.

The control panel has a plurality of buttons 110 and a tactile responsive display screen 109 for selectively controlling activation, access, and use of the camera module 106, the focusing mechanism, the light source, the temperature sensing mechanism, and the electronic components. When in use, as shown in FIG. 7, the display screen may simultaneously display the target of interest in the examination, the patient's temperature, battery level, current lens magnification, and the amount of memory available for images. The target of interest may include the eye structure, the ear canal, the nasal cavity, the throat, or any other examining feature of the patient. The power source has a battery and a removable adapter (not shown). The adapter is insertable into a USB port 111 on the housing 112. The adapter charges and operates the apparatus by connecting the adapter to the apparatus and to an electrical outlet or to an electronic device.

The housing 112 has a handle 113, a neck 114, and a head 115. The handle supports the removable battery therein. The handle has an accessible compartment to hold the battery. The neck supports the control panel. The head is supported by the neck of the housing. The head defines a recessed opening for supporting the display screen, a bore for receiving the temperature sensing mechanism, and a hole for receiving the charging adapter. The head contains (houses) the examining assembly, the light source, the temperature sensing mechanism, and the data processing mechanism.

In yet another embodiment, as also shown in the FIGS. 1-9, the invention is a handheld multipurpose medical diagnostic apparatus comprising (including or having) an examining assembly, a light source, a contactless temperature sensing mechanism, a data processing mechanism, a power source, and a housing. The examining assembly has a lens assembly has a rotatable circular plate and a plurality of lenses. The circular plate defines a plurality of spaced apart apertures arranged in a ring or circular pattern and an opening for circumscribing a speculum. Each of the apertures supports one of the plurality of lenses, and with each of the plurality of lenses having a different focal length or magnification for selectively magnifying, viewing, or examining at least a patient's face and body, the ear and ear canal, the structure of the eyes, the nasal cavity, and the throat during examination. The speculum has a proximal opening used as a viewpoint, the speculum engageable with a disposal examining tip. The speculum may be configured as a scope barrel.

The focusing mechanism is coupled to the lens assembly for rotating the circular plate for selectively switching to a different lens focal length, and for adjusting the focal length or magnification of each of the lens during examination, with the focusing mechanism operable by a direct drive stepper motor actuated by a control panel. The ease of changeability of lenses in this single diagnostic tool is distinguishable from existing separate single lens otoscopes and ophthalmoscopes. The camera module cooperates with the lens assembly for selectively capturing patient information comprising one or more images and video of the patient's face or body for a patient profile, and one or more images and video of the patient's ear canal, eye structure, nasal cavity, and throat during examination.

The light source has a plurality of illuminating members arranged in a circular pattern corresponding with the arrangement of the lens. The light source is capable of being used independently and selectively from the examining assembly. The light source is controlled by a control panel. The light source may have a plurality of LED illuminating members. The contactless infrared temperature sensor obtains a patient's temperature as data. The temperature sensor is in communication with the electronic components and the power source, with the temperature reading displayable on a display screen. The temperature sensor is actuated by a control panel. The apparatus may also include a rocker switch 117 for at least turning on the apparatus.

The data processing mechanism has a plurality of electronic components having memory capable of storing and retrieving the patient information and data obtained from the examining assembly and the temperature sensing mechanism; at least a microprocessor for processing the obtained the patient information and the data; a transmitter and a receiver for transmitting the patient information and data to and receiving from the patient information and data an external device. The transmission and receipt of the patient information and data may be transferred wired or wireless. The data processing mechanism further has a printed circuit board that is in electrical communication with the motor, the power source, the one or more of the electronic components, and the control panel.

The control panel has a plurality of buttons and a tactile responsible display screen (touch screen) for selectively controlling activation, access, and use of the camera module, the focusing mechanism, the light source, the temperature sensing mechanism, and the electronic components. The power source has a battery, and a removable adapter for charging and operating the apparatus by connecting the adapter to the apparatus and to an electrical outlet or to an electronic device. The adapter is further capable of transferring data to and from the apparatus to and from an external device.

The housing has a handle, a neck, and a head. The handle supports the battery therein. The handle of the housing has an attachment member for removably attaching the apparatus for storage or placement; a first hard surface; a second soft grip surface; and a tapered upper portion of the handle. The first hard surface is essentially a hard plastic. The second soft grip surface is a soft urethane grip surface. The handle is essentially bulbous at a lower portion of the handle as it curves inwardly and tapers upwardly into the neck. The attachment member is a metal lanyard hook 118 for removably attaching the apparatus to a hanging member. The neck is upwardly angled for additional support. The neck contains the control panel.

The head of the housing is supported by the neck. The head has a front and a back, and contains the examining assembly, the light source, the temperature sensor, and the data processing mechanism. The front of the housing head has the light source, the speculum, and the temperature sensor. The front of the housing head defines a hole for receiving the charging adapter, and a bore for receiving the temperature sensor. The back of the housing head has at least one indicator light, with the back of the housing head defining a recessed frame opening for supporting the display screen.

Those skilled in the art who have the benefit of this disclosure will appreciate that it may be used as the creative basis for designing devices or methods similar to those disclosed herein, or to design improvements to the invention disclosed herein; such new or improved creations should be recognized as dependent upon the invention disclosed herein, to the extent of such reliance upon this disclosure.

I claim:

1. A handheld multipurpose medical diagnostic apparatus comprising:
   a. an examining assembly comprising:
      i. a lens assembly having a plurality of lenses and a rotatable circular plate, with the rotatable circular plate defining a plurality of spaced apart apertures arranged in a ring pattern, each of the plurality of spaced apart apertures supporting one of the plurality of lenses, and with each of the plurality of lenses being selectively rotated with the rotatable circular plate to a desired lens wherein each of the plurality of lenses having a different focal length or magnification for selectively magnifying, viewing, or examining at least a patient's face and body, the ear and ear canal, the structure of the eyes, the nasal cavity, and the throat during viewing or examination
      ii. a speculum having a proximal opening for a viewpoint, with the speculum engageable with the lens assembly;
      iii. a focusing mechanism coupled to the lens assembly for rotating the rotatable circular plate with the plurality of lenses for selectively switching to a different lens focal length, and for adjusting the focal length or magnification of each of the lenses during examination, magnification, or viewing, with the focusing mechanism operable by a motor; and
      iv. a camera module for selectively capturing patient information comprising one or more images and video of the patient's face or body for a patient profile, and one or more images and video of the patient's ear canal, eye structure, nasal cavity, and throat;
      v. with the examining assembly being capable of being used selectively as an otoscope, an ophthalmoscope, and a camera;
   b. a light source capable of being used independently and selectively from the examining assembly, and with the light source being operatively controlled by a control panel;
   c. a contactless temperature sensing mechanism for obtaining a patient's body temperature as data, with the contactless temperature sensing mechanism being located below the lens assembly;
   d. a data processing mechanism having one or more electronic components being capable of storing, processing, and retrieving the patient information and data obtained from the examining assembly and the temperature sensing mechanism, and capable of transmitting and receiving the patient information and data to and from an external device;
   e. the control panel having a plurality of buttons and a tactile responsive display screen for selectively controlling activation, access, and use of the camera module, the focusing mechanism, the light source, the temperature sensing mechanism, and the electronic components;
   f. a power source comprising a battery, and a removable adapter for charging and operating the apparatus by connecting the removable adapter to the apparatus and to an electrical outlet or to an electronic device; and
   g. a housing comprising a handle, a neck, and a head;
      i. the handle supporting the battery therein;
      ii. the neck supporting the control panel; and
      iii. the head defining a recessed opening for supporting the display screen, a bore for receiving the temperature sensing mechanism, and a hole for receiving the removable adapter; with the head containing the examining assembly, the light source, the temperature sensing mechanism, and the data processing mechanism, with the temperature sensing mechanism being located below the lens assembly, the speculum, and the light source.

2. The handheld multipurpose medical diagnostic apparatus of claim 1, at least a first of the plurality of lens being a single 3× lens, and at least a second of the plurality of lens being a single 15× lens.

3. The handheld multipurpose medical diagnostic apparatus of claim 1, the motor being a direct drive stepper motor controlling the lens assembly and selectively actuated by the control panel.

4. The handheld multipurpose medical diagnostic apparatus of claim 1, the contactless temperature sensing mechanism comprising an infrared sensor in communication with the electronic components and the power source, with a temperature reading displayable on the display screen, and with the temperature sensing mechanism actuated by the control panel.

5. The handheld multipurpose medical diagnostic apparatus of claim 1, the data processing mechanism further comprising the one or more electronic components comprising memory capable of storing and retrieving patient information and data obtained from the examining assembly and the temperature sensing mechanism; at least a microprocessor for processing the obtained patient information, the data obtained from the examining assembly, and the data obtained from the temperature sensing mechanism; a transmitter and a receiver each having a signal for transmitting the patient information and data to and receiving the patient information and the data from the external device, wherein the transmission and receipt of the patient information and the data may be transferred wirelessly or wired with the removable adapter; and a printed circuit board being in communication with the motor, the power source, the one or more of the electronic components, and the control panel.

6. The handheld multipurpose medical diagnostic apparatus of claim 5, the data processing mechanism providing review of patient information and data on the display screen directly from the apparatus memory.

7. The handheld multipurpose medical diagnostic apparatus of claim 5, the data processing mechanism providing review of patient information and data from an external device on the display screen.

8. The handheld multipurpose medical diagnostic apparatus of claim 1, the head of the housing further being offset and upstanding from the neck, with the head and a substantial portion of the neck overhanging the handle.

9. A handheld multipurpose medical diagnostic apparatus comprising:
  a. an examining assembly comprising:
    i. a lens assembly having a plurality of lenses and a rotatable circular plate, with the rotatable circular plate defining a plurality of spaced apart apertures arranged in a ring pattern and defining an opening for circumscribing a speculum, each of the plurality of spaced apart apertures supporting one of the plurality of lenses, and with each of the plurality of lenses being selectively rotated with the rotatable circular plate to a desired lens wherein each of the plurality of lenses having a different focal length or magnification for selectively magnifying, viewing, or examining at least a patient's face and body, the ear and ear canal, the structure of the eyes, the nasal cavity, and the throat during viewing or examination, and with the speculum having a proximal opening used as a viewpoint, the speculum engageable with a disposal examining tip;
    ii. a focusing mechanism coupled to the lens assembly for rotating the rotatable circular plate with the plurality of lenses for selectively switching to a different lens focal length, and for adjusting the focal length or magnification of each of the lenses during examination, magnification, or viewing, with the focusing mechanism operable by a direct drive stepper motor actuated by a control panel; and
    iii. a camera module cooperating with the lens assembly for selectively capturing patient information comprising one or more images and video of the patient's face or body for a patient profile, and one or more images and video of the patient's ear canal, eye structure, nasal cavity, and throat during examination;
  b. a light source capable of being used independently and selectively from the examining assembly, with the light source being controlled by the control panel;
  c. a contactless, infrared temperature sensor for obtaining a patient's temperature as data, with the temperature sensor being in communication with one or more electronic components of a data processing mechanism and the power source, with a temperature reading displayable on a display screen, with the temperature sensor being located below the lens assembly, and with the temperature sensor being actuated by the control panel;
  d. the data processing mechanism comprising:
    i. the one or more electronic components comprising memory capable of storing and retrieving the patient information and data obtained from the examining assembly and the temperature sensing mechanism; at least a microprocessor for processing the obtained patient information, the data obtained from the examining assembly, and the data obtained from the temperature sensing mechanism; a transmitter and a receiver for transmitting the patient information and data to and receiving the patient information and data from an external device, wherein the transmission and receipt of the patient information and data may be transferred wired or wireless; and
    ii. a printed circuit board in electrical communication with the motor, a power source, the one or more of the electronic components, and the control panel;
  e. the control panel having a plurality of buttons and a tactile responsive display screen for selectively controlling activation, access, and use of the camera module, the focusing mechanism, the light source, the temperature sensing mechanism, and the electronic components;
  f. the power source comprising a battery, and a removable adapter for charging and operating the apparatus by connecting the removable adapter to the apparatus and to an electrical outlet or to an electronic device, with the removable adapter further capable of transferring data to and from the apparatus to and from an external device; and
  g. a housing comprising a handle, a neck, and a head;
    i. the handle of the housing comprising an attachment member for removably attaching the apparatus for storage or placement; a first hard surface; a second soft grip surface; and a tapered upper portion of the handle, with the handle supporting the battery therein;
    ii. the neck being upwardly angled of the housing comprising the control panel; and
    iii. the head defining a recessed frame opening for supporting the display screen, a bore for receiving the temperature sensor, and a hole for receiving the removable adapter; with the head containing the examining assembly, the light source, the temperature sensor, and the data processing mechanism, with the temperature sensor being located below the lens assembly, the speculum, and the light source.

10. The handheld multipurpose medical diagnostic apparatus of claim 9, the speculum further configured as scope barrel.

11. The handheld multipurpose medical diagnostic apparatus of claim 9, the light source further comprising a plurality of LED illuminating members around in a circular pattern coinciding with the plurality of lenses.

12. The handheld multipurpose medical diagnostic apparatus of claim 9, at least a first of the plurality of lens being a single 3× lens, and at least a second of the plurality of lens being a single 15× lens.

13. The handheld multipurpose medical diagnostic apparatus of claim 9, the apparatus further comprising a rocker switch member for turning on the apparatus.

14. The handheld multipurpose medical diagnostic apparatus of claim 9, the head of the housing further being offset and upstanding from the neck, with the head and a substantial portion of the neck overhanging the handle.

* * * * *